United States Patent
Fieselmann

(10) Patent No.: US 10,169,867 B2
(45) Date of Patent: Jan. 1, 2019

(54) EVALUATION OF AN X-RAY IMAGE OF A BREAST PRODUCED DURING A MAMMOGRAPHY

(71) Applicant: SIEMENS HEALTHCARE GMBH, Erlangen (DE)

(72) Inventor: Andreas Fieselmann, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/308,135

(22) PCT Filed: Mar. 3, 2015

(86) PCT No.: PCT/EP2015/054429
§ 371 (c)(1),
(2) Date: Nov. 1, 2016

(87) PCT Pub. No.: WO2015/169470
PCT Pub. Date: Nov. 12, 2015

(65) Prior Publication Data
US 2017/0053403 A1 Feb. 23, 2017

(30) Foreign Application Priority Data
May 6, 2014 (DE) .................. 10 2014 208 411

(51) Int. Cl.
*G06T 7/00* (2017.01)
*A61B 5/00* (2006.01)

(52) U.S. Cl.
CPC .......... *G06T 7/0012* (2013.01); *A61B 5/4312* (2013.01); *G06T 2207/10116* (2013.01); *G06T 2207/20036* (2013.01); *G06T 2207/30068* (2013.01)

(58) Field of Classification Search
CPC ......... G06T 7/0012; G06T 2207/10116; G06T 2207/20036; G06T 2207/30068; A61B 5/4312
See application file for complete search history.

(56) References Cited

U.S. PATENT DOCUMENTS 5,657,362 A 8/1997 Giger et al.
6,282,305 B1 * 8/2001 Huo ...................... G06T 7/0012
382/128
(Continued)

FOREIGN PATENT DOCUMENTS

CN 101664318 A 3/2010
CN 101849836 A 10/2010
(Continued)

OTHER PUBLICATIONS

ACR BI-RADS Atlas—Mammography II. Reporting System American College of Radiology, pp. 121-140, 2013.
(Continued)

*Primary Examiner* — Mekonen Bekele
(74) *Attorney, Agent, or Firm* — Lempia Summerfield Katz LLC

(57) ABSTRACT

The embodiments relate to a method, an apparatus, and a computer program for evaluating an x-ray image of a breast produced during a mammography. In order to simplify the evaluation of such an x-ray image in respect of the breast density, a method is proposed to automatically determine the masking risk caused by the mammographically dense tissue and to use this for categorizing, describing, and/or representing the breast density.

12 Claims, 6 Drawing Sheets

(56) References Cited

U.S. PATENT DOCUMENTS

| | | | |
|---|---|---|---|
| 7,664,604 B1* | 2/2010 | Heine | G06F 19/00 |
| | | | 702/19 |
| 2004/0252870 A1* | 12/2004 | Reeves | G06T 7/0012 |
| | | | 382/128 |
| 2004/0258310 A1* | 12/2004 | Giger | G06T 7/0012 |
| | | | 382/190 |
| 2005/0273009 A1* | 12/2005 | Deischinger | A61B 8/00 |
| | | | 600/437 |
| 2008/0114234 A1* | 5/2008 | Gering | G01R 33/546 |
| | | | 600/411 |
| 2009/0171236 A1* | 7/2009 | Davies | A61B 5/0537 |
| | | | 600/547 |
| 2010/0158332 A1 | 6/2010 | Rico | |
| 2010/0246924 A1 | 9/2010 | Morita | |
| 2010/0321404 A1 | 12/2010 | Fischer et al. | |
| 2011/0013819 A1* | 1/2011 | Raundahl | G06K 9/527 |
| | | | 382/132 |
| 2011/0026791 A1* | 2/2011 | Collins | G06K 9/62 |
| | | | 382/131 |
| 2012/0020536 A1 | 1/2012 | Moehrle | |
| 2013/0251104 A1 | 9/2013 | Roessl et al. | |
| 2013/0293569 A1* | 11/2013 | Lee | G01S 15/8984 |
| | | | 345/619 |
| 2014/0037044 A1 | 2/2014 | Ning et al. | |

FOREIGN PATENT DOCUMENTS

| | | |
|---|---|---|
| CN | 102438529 A | 5/2012 |
| CN | 102956035 A | 3/2013 |
| CN | 103220974 A | 7/2013 |
| CN | 103347447 A | 10/2013 |
| CN | 103582455 A | 2/2014 |
| DE | 102006021042 A1 | 10/2007 |
| DE | 102006051778 A1 | 5/2008 |

OTHER PUBLICATIONS

Colin, et al., "Can mammographic assessments lead to consider density as a risk factor for breast cancer?", European Journal of Radiology; Elsevier Science; NL; Bd. 82; Nr. 3; pp. 404-411; 2010.
German office Action for related German Application No. 10 2014 208 411.3 dated Dec. 2, 2014, with English Translation.
PCT International Search Report and Written Opinion of the International Searching Authority dated Jun. 5, 2015 for corresponding PCT/EP2015-054429, with English Translation.
Van Engeland, et al., "Volumetric Breast Density Estimation From Full-Field Digital Mammograms," IEEE Transactions on Medical Imaging, vol. 25, No. 3., pp. 273-282, Mar. 2006.
Chinese Office Action for Chinese Application No. 201580023258.6 dated Oct. 16, 2018.

* cited by examiner

12

EVALUATION OF AN X-RAY IMAGE OF A BREAST PRODUCED DURING A MAMMOGRAPHY

The present patent document is a § 371 nationalization of PCT Application Serial Number PCT/EP2015/054429, filed Mar. 3, 2015, designating the United States, which is hereby incorporated by reference, and this patent document also claims the benefit of DE 10 2014 208 411.3, filed May 6, 2014, which is also hereby incorporated by reference.

TECHNICAL FIELD

The embodiments relate to a method, an apparatus, and a computer program for evaluating an x-ray image of a breast produced during mammography.

BACKGROUND

Automatically calculating the volumetric breast density (VBD) from an x-ray image produced during mammography is known. The volumetric breast density is defined as the ratio of the volume of the fibroglandular tissue to the overall volume of the breast. Below, the terms "fibroglandular tissue," "glandular tissue," and "mammographically dense tissue" or "dense tissue" are used synonymously. On the basis of this VBD value, the breast has until now been assigned a specific breast density category using fixed thresholds, e.g., a BI-RADS value from "1" to "4" according to the classification by the American College of Radiology (ACR). By way of example, this is described in U.S. Patent Publication No. 2011/0026791 A1 and in DE 10 2006 021 042 A1.

Women whose breast has a high VBD value have an increased risk of getting breast cancer. The increase in this risk is partly traced back to the fact that cancerous tissue is masked by mammographically dense tissue and therefore it is not identified during mammography.

It is known that the masking risk does not always correlate with the VBD value. FIGS. 1 and 2 depict a breast 3 compressed between two plates 1, 2 during mammography. After passing through the tissue of the breast 3, x-ray radiation 5 emanating from an x-ray source 4 is incident on an x-ray detector 6. As depicted in FIGS. 1 and 2, the same volume of fibroglandular tissue 7, 8 may cover small masses 9 in different ways. In the example depicted in FIG. 1, the fibroglandular tissue 7, which has a specific volume, is localized at a single position such that the small mass 9 is covered by the dense tissue 7. As a result of the volume of the fibroglandular tissue 7, the depicted region of the breast 3 is characterized by a specific VBD value. By contrast, the fibroglandular tissue 8, which has an identical volume, is distributed more uniformly in the volume of the breast 3 in the example depicted in FIG. 2, and so it is less likely for the small mass 9 to be covered by the dense tissue 8. Despite the VBD values being identical, the risk of masking of the small mass 9 is lower in FIG. 2. Therefore, the sole use of the VBD value is not sufficient for an accurate description of the masking effect by mammographically dense tissue 7, 8.

It is for this reason that the 5th edition of the ACR BI-RADS Atlas proposes new categories "a" to "d" with a verbal description of the breast density category, defined by the visually estimated portion of fibroglandular tissue in the breast. Taking into account the masking risk was proposed for the first time in this context. Thus, the category "c" may be assigned if small masses may be obscured as a result of a heterogeneous density distribution. It is proposed that the radiologist in such a case describes the position of the dense tissue in a further sentence.

Moreover, the nature of the breast may be described with the category "a" if the breasts are almost entirely fatty. The category "b" may be present if there are scattered areas of fibroglandular density. The category "d" may be assigned if the breasts are extremely dense, which lowers the sensitivity of mammography.

As depicted in FIG. 3, a glandularity map was previously calculated in act 101 using the x-ray image produced during mammography, with the glandularity denoting the proportion of the fibroglandular tissue in the overall tissue. The glandularity map defines the amount of glandular tissue in each image pixel of the x-ray image, either as a specification in millimeters or as a percentage specification, with the value lying in a range from, e.g., 1% to 50%. Then, the mean glandularity, the VBD value, is established in act 102. Subsequently, the categories "a" to "d" are determined in act 103 based purely on the VBD value. The acts are carried out either manually by a radiologist or already in an automated form with the aid of available systems. However, only experienced radiologists may undertake a reliable assessment of the masking risk and generate a complete breast density report, taking into account the masking risk, in accordance with the prescriptions of the ACR. Here, there is a risk of errors of judgment.

SUMMARY AND DESCRIPTION

The scope of the present invention is defined solely by the appended claims and is not affected to any degree by the statements within this summary. The present embodiments may obviate one or more of the drawbacks or limitations in the related art.

It is therefore an object to enable a more precise evaluation of an x-ray image of a breast, produced during mammography, in respect of the breast density. This object is achieved by a method, an apparatus, or a computer program described herein. The advantages and embodiments explained below in conjunction with the method apply analogously to the apparatus as well, and vice versa.

The embodiments proceed from taking the masking properties of the fibroglandular tissue into account to a greater extent when determining the breast density. A core concept lies in undertaking the evaluation of the x-ray image taking into account the masking risk and undertaking it in a largely, (e.g., completely), automated manner. To this end, the masking risk caused by mammographically dense tissue is determined automatically and used for categorizing, describing and/or representing the breast density. A clinically applicable, standardized method for simple and improved description of the breast density is provided by the automatic quantification of the masking risk.

In one embodiment, a masking risk map for the region of the breast depicted in the x-ray image is produced automatically to this end. On the basis thereof, a masking risk value (M value) may be produced automatically, the masking risk value quantifying the masking risk for the region of the breast depicted in the x-ray image. Advantageously, this M value is used in conjunction with the VBD value already used previously in order to determine a breast density category in accordance with the 5th edition of BI-RADS in a more precise manner.

In one embodiment, the produced masking risk map is displayed on a screen together with the x-ray image in order to display those regions of the image for which an increased masking risk was established. A radiologist may use the information in respect of the masking risk in order to concentrate on these regions during the evaluation of the x-ray image.

A description of the position and/or the distribution of mammographically dense tissue for the region of the breast depicted in the x-ray image is produced automatically on the basis of the masking risk map in an embodiment, advantageously in the form of a short sentence as may be used as part of the breast density report in accordance with the 5th edition of BI-RADS.

It is particularly advantageous if some or all of the applications specified above are combined with one another.

As disclosed herein, it is possible, for the first time, to generate a quantified, automatically generated breast density report taking into account the masking risk, which breast density report meets the requirements of the 5th edition of BI-RADS. The accuracy of the classification into the breast density categories to be undertaken is increased in relation to conventional solutions. Subjective influences and errors are reduced or precluded. The evaluation is carried out in a consistent and reproducible manner. Overall, what is achieved is a very much simpler evaluation of an x-ray image of the breast, produced during mammography, in respect to the breast density.

The embodiments are applicable in a particularly advantageous manner in the case of digital mammography devices and in the field of image-assisted, e.g., automated breast density measurements.

BRIEF DESCRIPTION OF THE DRAWINGS

The above-described properties, features and advantages, and the manner in which they are achieved, become more clear and more easily understandable in conjunction with the following description of exemplary embodiments, which are explained in more detail in conjunction with the drawings.

All of the figures depict the embodiments in a schematic manner. Here, the same reference signs correspond to elements with the same or a comparable function.

DETAILED DESCRIPTION

The masking risk caused by mammographically dense tissue 7, 8 is determined automatically and used for categorizing, describing and/or representing the breast density in the method for evaluating an x-ray image 10 of a breast 3 produced during mammography. The x-ray image 10 to be evaluated may be a full-field mammography (FFDM) image or a projection image from a digital breast tomosynthesis (DBT) record.

If reference is made below to an "x-ray image", this need not relate to the whole record. Instead, this may also only relate to a currently displayed or processed image region of the recorded x-ray image.

Figure 1:
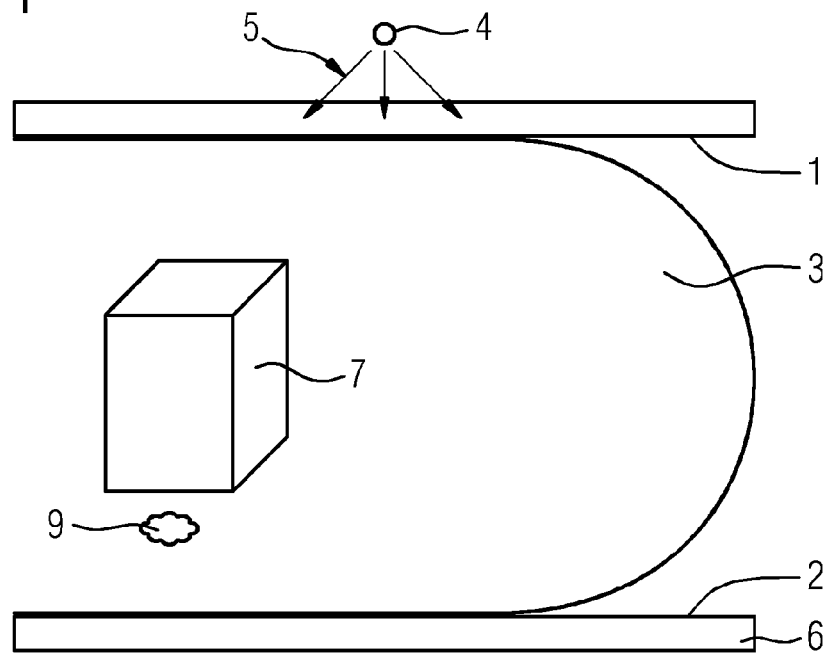
FIGS. 1 and 2 depict an illustration of the masking effect of relatively small masses by differently arranged fibroglandular tissue.
Figure 2:
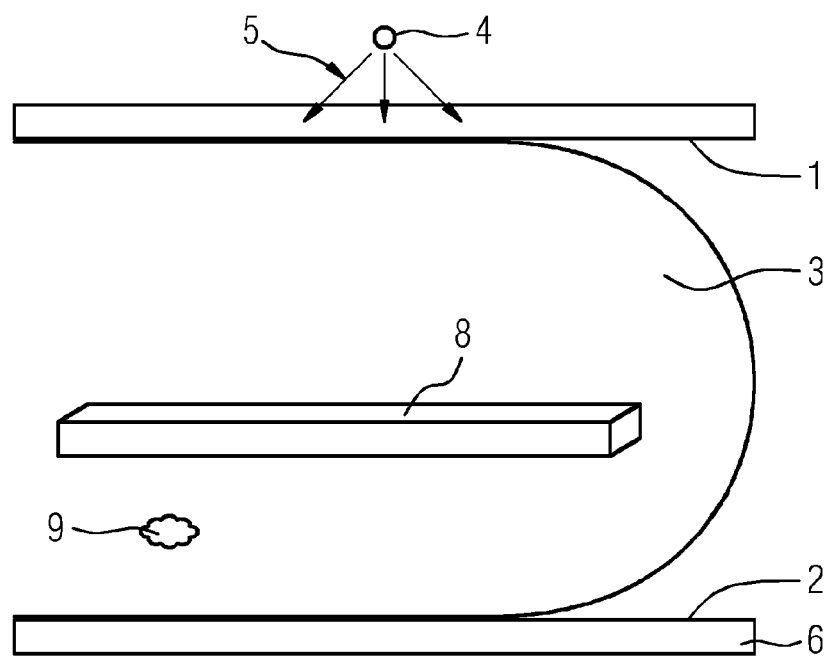
Figure 3:
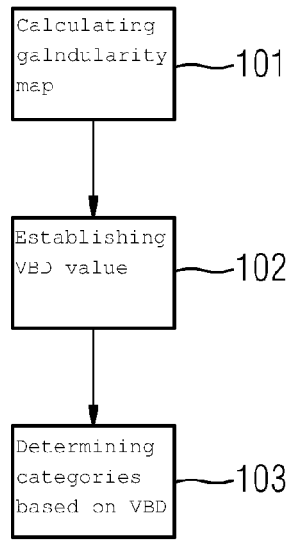
FIG. 3 depicts the conventional procedure when generating a breast density report (prior art).
Figure 4:
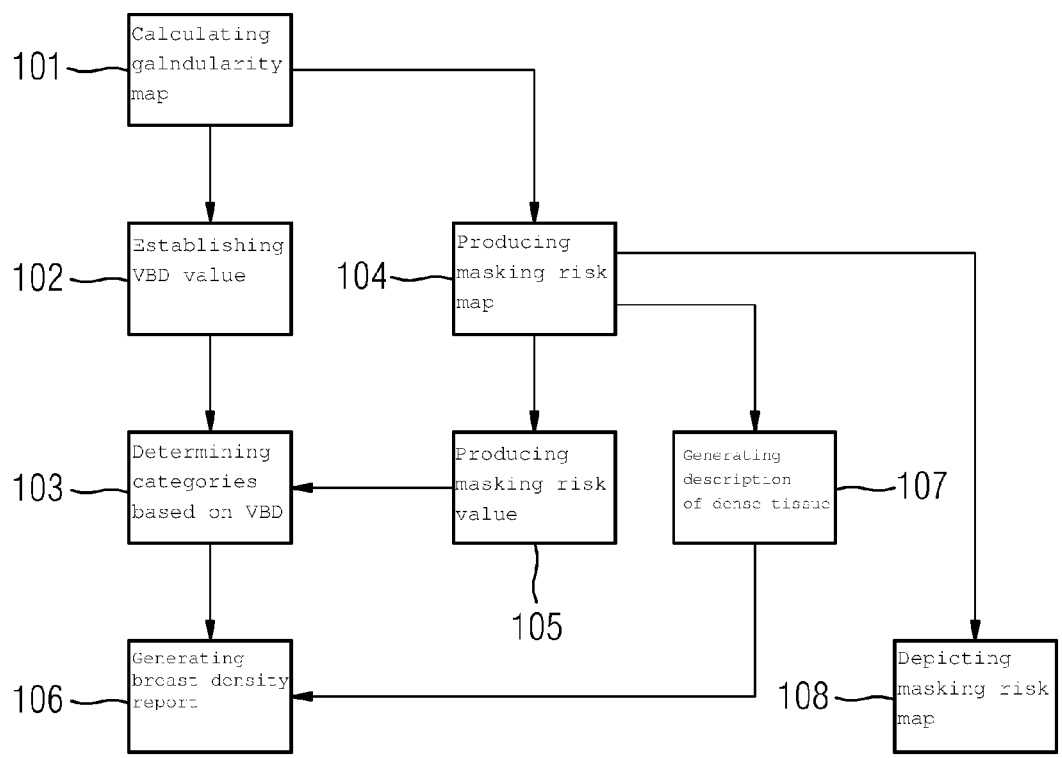
FIG. 4 depicts the procedure when generating a breast density report in accordance with an example.

The basis of the method is the automatic production of a masking risk map 11 for the region of the breast 3 depicted in the x-ray image; see FIG. 4, act 104. This masking risk map 11 depicts the interconnected, dense tissue. Below, an exemplary way for producing such a masking risk map 11 is described.

Figure 5:
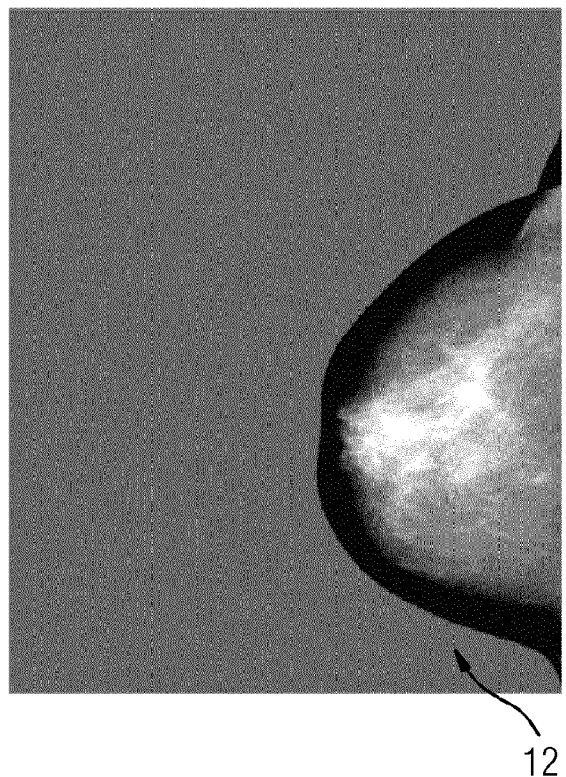
FIG. 5 depicts a glandularity map of a breast according to an example.

The data from a glandularity map 12 (G(x,y)) as depicted in an exemplary manner in FIG. 5 serves as input data for establishing the masking risk map 11. In the subsequent description, the assumption is made that the glandularity is specified in percent. A conversion of the glandularity into millimeter (mm) units may easily be carried out by multiplying the percentage by the known thickness of the compressed breast, measured in mm. Furthermore, the assumption is made that structures that are not relevant to calculating the breast density, such as the pectoral muscle or the mammilla, were segmented and removed from the glandularity map 12.

There are various options, known to a person skilled in the art, for calculating such a glandularity map 12. The manner of the calculation of the glandularities is not a component disclosed herein. Instead, the present embodiments relate to the evaluation of the glandularity map 12, as described in more detail below.

When calculating the masking risk map 11, the glandularity map 12 is processed a number of times at different threshold planes in the sub-acts 104a, 104b and 104c of act 104 (not depicted individually in FIG. 4). The number of run-throughs depends in this case on the number of desired threshold planes. By way of example, a first threshold plane includes breast density values between 10% and 15% and a second threshold plane includes breast density values between 15% and 20%, etc. Here, the threshold planes may overlap. In the subsequent example, the first threshold plane includes breast density values above 15%, the second threshold plane includes breast density values above 20%, and the third threshold plane includes breast density values above 25% (N=3). The sub-acts 104a, 104b and 104c are carried out N times (i=1, . . . , N), once for each threshold plane.

Figure 6:
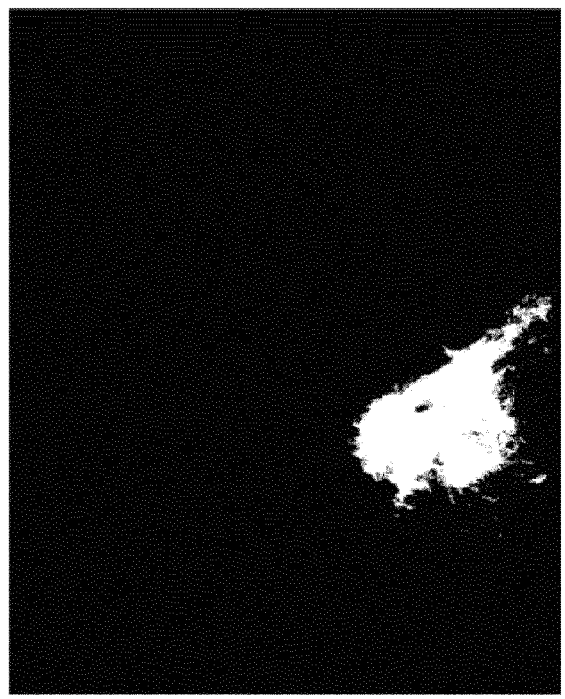
FIG. 6 depicts an image of a breast after a threshold treatment according to an example.

In the first sub-act 104a, there is a binary segmentation into a foreground and background region. Here, the binary image $I_i^{sg}(x,y)$ is produced by a threshold treatment of the glandularity map 12 with the threshold $T_i=\{15\%; 20\%; 25\%\}$. Here, the assumption is made that the T-values are sorted in an increasing sequence, e.g., the threshold planes represent regions with increasing density. Hence, all image pixels, in which the density is greater than the given threshold $T_i$ are marked in the produced image $I_i^{sg}(x,y)$. At the locations of these image pixels, there is a potential risk of small masses 9 being obscured. FIG. 6 depicts an image $I_1^{sg}(x,y)$ in an exemplary manner.

Figure 7:
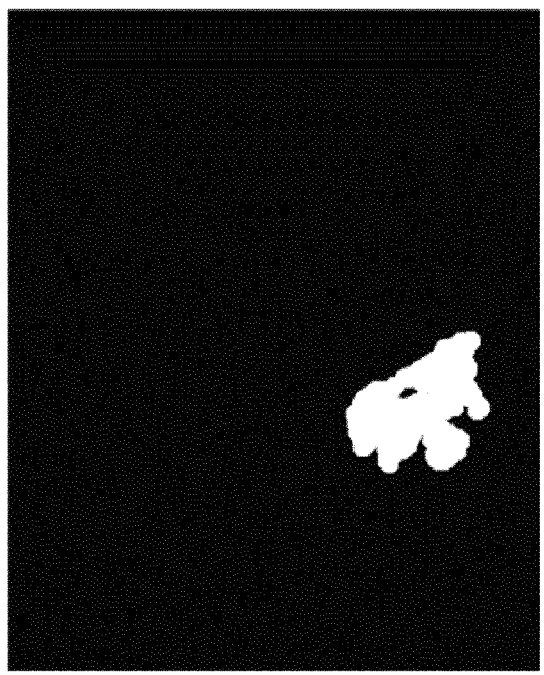
FIG. 7 depicts an image of a breast after a morphological opening according to an example.

However, until now the connectivity of the dense tissue remained unaccounted for. This is of importance here since a small isolated region of dense tissue with a glandularity greater than or equal to the threshold $T_i$ may be segmented in the employed approach of the threshold treatment; nevertheless, it is in fact too small to actually obscure a small mass 9. The connectivity of the dense tissue is therefore also taken into account during the production of the masking risk map 11. This is carried out by virtue of a morphological opening method being applied in the sub-act 104b following this. Here, the image $I_i^{op}$ (x,y) is calculated by morphological opening of the image $I_i^{sg}$(x,y) with a disk-shaped structure element with the radius $R_i$. By way of this sub-act, comparatively small isolated regions of dense tissue, in which it is unlikely that they obscure small masses 9 on account of the size thereof, are removed. Here, a disk-shaped structure element is used since the assumption is made that the masses 9 primarily have a round form. FIG. 7 depicts an image $I_1^{op}$ (x,y) in an exemplary manner.

The application of this sub-act is also of particular advantage because this also allows small, isolated, contrast-rich objects, such as e.g. microcalcification or metal clips, which may be contained in the glandularity map 12, to be removed.

It is particularly advantageous if, during the morphological opening method, the same structure elements are used for the removal and for the renewed addition, as this is already implemented as a standard method in software libraries. In the example, the radius $R_i$={0.4 cm; 0.4 cm; 0.4 cm}. It is likewise possible to use disk-shaped structure elements with different radii for the removal and the addition. It is particularly advantageous if the radius for the addition is less than that for removal because then the final area is slightly smaller than the original area. As a result, it is possible to remove regions in which some of the mass lies in a dense region but another part of the mass lies outside of the dense region, and so there merely is the risk of less-critical partial masking. Advantageously, a structure element is used in this context for the addition, the radius of which corresponds to a certain fraction of the radius of that structure element used for the removal. It was found to be particularly advantageous if the radius of the structure element used for the addition corresponds to a value of 70% to 80% of the radius of the structure element used for the removal.

In the sub-act 104c, the area $A_i$ of the remaining foreground region in the image $I_i^{op}$(x,y) is calculated, e.g., the area of that region having such image pixels in which the density is greater than the respective threshold. This area $A_i$ (with units of cm²) is a measure for the risk for the respective threshold plane that the dense tissue covers a small mass 9. By way of example the area depicted in FIG. 7 is $A_1$=13.5 cm². The further areas are, e.g., $A_2$=6.3 cm² and $A_3$=3.1 cm².

Figure 9:
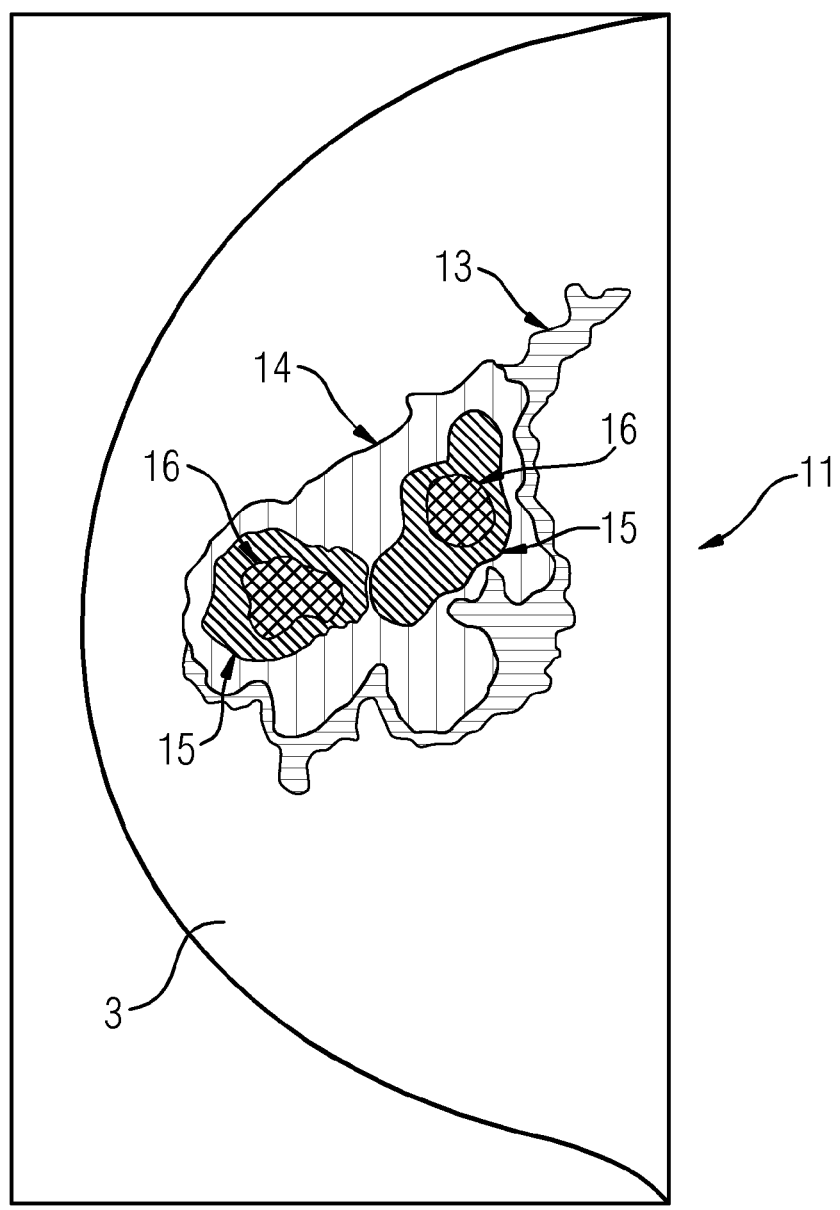
FIG. 9 depicts a masking risk map according to an example.

Using the obtained images $I_i^{op}$(x,y) with i=1, . . . , N, the two-dimensional masking risk map 11 is generated in sub-act 104d of the act 104 (which is likewise not depicted in detail in FIG. 4) after running through the sub-acts 104a to 104c repeatedly, in which masking risk map the largest possible value i from the image set $I_i^{op}$(x,y), at which the image pixel is still segmented, e.g., classified as foreground region, is assigned to each image pixel (x,y). An example for such a masking risk map 11 is depicted in FIG. 9. On the breast depicted in dark blue, the glandularity map 12 of which is depicted in FIG. 5, dense breast tissue 13, which remained unconsidered during the evaluation of the masking risk due to the restricted connectivity thereof, is depicted in light blue. Dense tissue 14 with a glandularity above 15% is depicted in yellow, dense tissue 15 with a glandularity above 20% is depicted in orange and dense tissue 16 with a glandularity above 25% is depicted in red. A different color coding may be used.

Subsequently, a masking risk value (M value) 17 is automatically produced for the region of the breast depicted in the x-ray image 10; see FIG. 4, act 105. This M value 17 quantifies the masking risk for this region of the breast 3.

Here, a low M value 17 means that the probability of a mass 9 being masked is low, while a high M value 17 means a high masking probability. By way of example, in the case of a high M value 17, the radiologist may recommend carrying out a further examination, for example, a breast ultrasound examination or a breast tomosynthesis. An exemplary way for producing such an M value 17 is described below.

In a first sub-act 105a, the calculated areas $A_i$ are used to calculate a (dimensionless) overall risk value (ρ) 18. By way of example, this is carried out by applying a linear risk model:

$$\rho = \frac{1}{N}\sum_{i=1}^{N} c_i A_i$$

where the coefficients $c_i$ have increasing (or at least not decreasing) values, which are $c_i$={2 cm⁻²; 5 cm⁻²; 8 cm⁻²} in the example. As a result of this weighted summation, the areas with a higher density contribute more strongly to the overall risk. In the example described here, ρ=2.52. Instead of a linear risk model, it is also possible to use other, e.g., nonlinear models.

Since the interpretation of the overall risk value p is easier if the value is mapped to a numerical scale from 0% to 100%, there is a normalization in the subsequent sub-act 105b using the mapping function (f) 21, as a result of which the masking risk value (M) 17 is generated. Here, M=f(ρ) applies.

Figure 8:
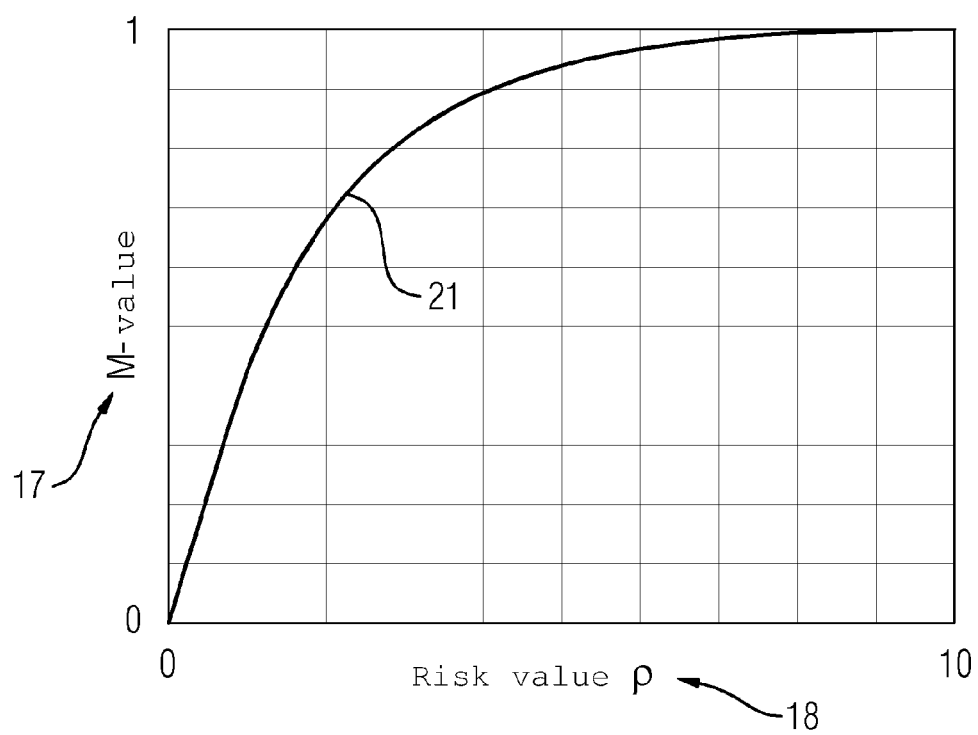
FIG. 8 depicts a representation of a mapping function f, as is used for calculating the M value, according to an example.

The mapping function 21 may be a nonlinear function f(ρ)=1−exp(−αρ), where α=0.57, as depicted in FIG. 8. An advantage of such a nonlinear function is that the behavior thereof is approximately piecewise linear. Here, the function is increasing in such a way that the increasing p values lead to ever larger M values, and the function asymptotically reaches 100%. However, it is also possible to use other mapping functions f. In the example described here, M=74%.

Subsequently, the M value 17 is used to assign a breast density category 20 to the region of the breast depicted in the x-ray image 10; see FIG. 4, act 103. The assignment may be carried out in a fully automated manner. In another embodiment, the assignment also takes place in a semi-automated manner. This means that a proposition is automatically presented to the radiologist, which the radiologist may agree with or which the radiologist may modify.

The assignment of a breast density category 20 to the x-ray image 10 is carried out using and by linking the VBD value 19, which may lie in a range between 2% and 30%, and the M value 17, which may assume a value between 0% and 100%. Since the assumption may be made that low VBD values 19 lead to low M values 17 and high VBD values 19 lead to high M values 17, it is expedient to use the M value 17 when assessing the mean value range of the VBD values 19. Here, distinguishing between the two breast density categories "b" and "c" is of particular importance since the two categories "c" and "d" each relate to "dense" breasts and an additional examination is recommendable according to the current guidelines.

Figure 10:
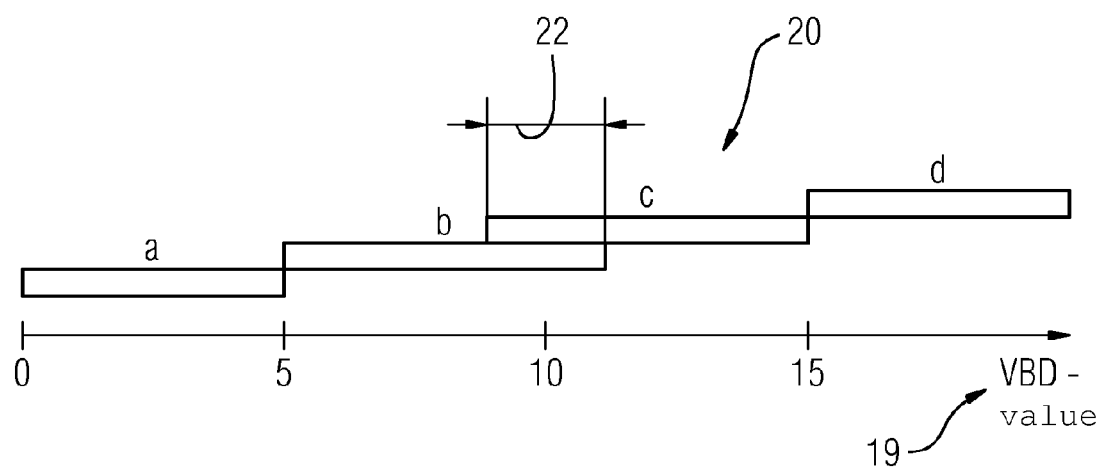
FIG. 10 depicts a representation of the VBD values in relation to breast density categories according to an example.
Figure 11:
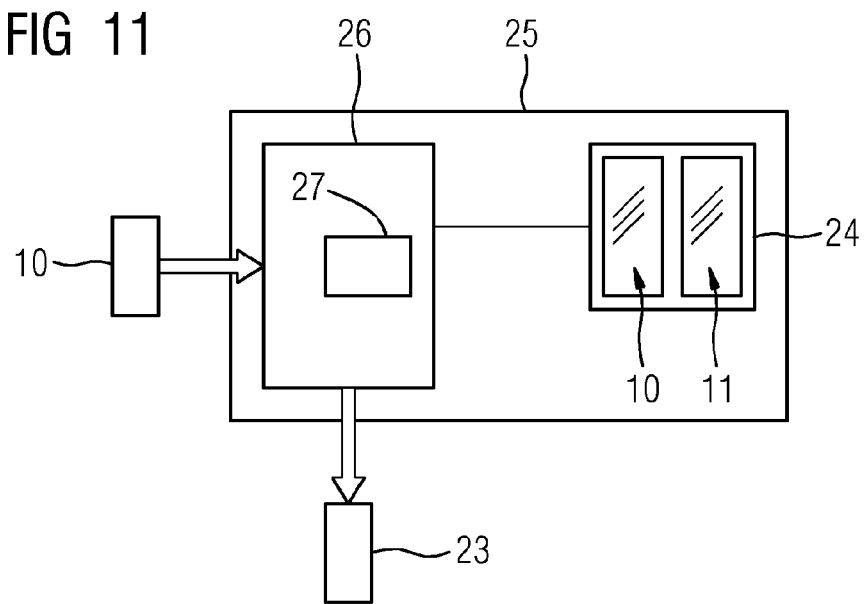
FIG. 11 depicts an apparatus according to one example.

Therefore, it is proposed to use the M value 17 in such a way that it only influences the assignment of the breast density categories "b" and "c". FIG. 10 illustrates the region 22 of the VBD value 19 in which the M value 17 may influence the classification into the individual breast density categories "a" to "d". Here, instead of using a sharp VBD threshold of e.g. 10% for distinguishing between adjacent categories "b" and "c", as was conventional up until now, a flexible threshold is proposed for delimiting these two breast density categories 20. By way of example, this flexible threshold may extend over a range 22 of VBD values 19 from 9.2% to 10.8%.

The table below clarifies, in an exemplary manner, the assignment of a specific breast density category 20 in a manner dependent on the respective M value 17 in the case of virtually identical VBD values 19 in this threshold region 22.

| VBD value | M value | Breast density category |
|-----------|---------|-------------------------|
| 9.2%      | 88%     | c                       |
| 9.4%      | 23%     | b                       |
| 10.2%     | 23%     | b                       |
| 10.7%     | 54%     | c                       |

The use of other decision rules is possible. It is also possible for other factors, such as, e.g., the age of the woman, to be included in the classification.

At the same time as calculating the M value 17, a description of the position and/or the spatial distribution of mammographically dense tissue is generated automatically on the basis of the masking risk map 11 for the region of the breast 3 depicted in the x-ray image 10, e.g., the description is generated using the map; see FIG. 4, act 107. This relates in particular to the spatial arrangement of those regions 14, 15, 16 having a very high masking risk; see the regions 16 depicted in red in FIG. 9. The masking risk map 11 is automatically analyzed with the aid of a suitable algorithm and a corresponding description in text form, for example in the form of a short sentence, is generated and added to the breast density report 23. Here, a standardized form of a verbal description is advantageous, for example using a subdivision of the image into quadrants.

A correct breast density report 23 in accordance with the prescriptions from the ACR is generated in act 106 together with the breast density categories 20 determined in act 103 and the position descriptions generated in act 107.

In parallel thereto, the masking risk map 11, see FIG. 9, is depicted for the radiologist on a screen 24 together with the x-ray image 10; see FIG. 4, act 108. The radiologist may use this information to, e.g., be able to better evaluate the automatically generated suggestion of a breast density category 20 in act 103.

Here, the masking risk map 11 may be depicted next to the (processed) FFDM image or the reconstructed DBT data record, or the masking risk map 11 may be fused with the FFDM image or the DBT data record. By way of example, the FFDM image or the DBT data record may be converted into the HSV color space. In this color space, grayscale value information is stored in the "V" channel. The two other channels "H" and "S" serve to encode the masking risk map 11. By changing the values in these two channels, it is possible in a simple manner to control the display strength of the masking risk map 11 as an overlay on the FFDM image or the DBT data record. In this manner, the radiologist may particularly easily superimpose or mask the masking risk map 11 on/from the x-ray image 10. However, a change between the two views in the case of the superposition of the images or maps may also be brought about in a different way.

The values of the parameters (N, $T_i$, $R_i$, $c_i$) described in the described exemplary embodiment may be made dependent on other parameters, for example on the compressed breast thickness or on irradiation parameters.

If the x-ray image is a DBT record, n=25 recorded images may be present, with, e.g., each projection image being evaluated individually. Likewise, the information obtained from all n projections may be used to calculate a common masking risk map 11, a common VBD value 21, and a common M value 17. Here, use may be made of, e.g., a (weighted) averaging with removal of the outliers.

The apparatus 25 is embodied to carry out the described method. The apparatus may include a data processing unit 26, which is embodied to carry out all acts related to the processing of data in accordance with the method described here. The processing unit 26 may have a plurality of functional modules, wherein each functional module is embodied to carry out a specific function or a plurality of specific functions in accordance with the described method. By way of example, the apparatus 25 has a screen 24 for displaying the x-ray image 10 and/or the masking risk map 11. Suitable input and output devices are likewise provided, such as interfaces for entering the x-ray image 10 and for outputting the breast density report 23.

The functional modules may be hardware modules or software modules. Expressed differently, the embodiment, to the extent that the embodiment relates to the processing unit 26, may be implemented in the form of computer hardware or in the form of computer software or in a combination of hardware and software. To the extent that the embodiment is implemented in the form of software, e.g., as a computer program 27, all described functions are realized by computer program instructions when the computer program 27 is executed on a computer 26 with a processor. Here, the computer program instructions are implemented in a manner known per se in any programming language and may be provided to the computer in any form, for example, in the form of data packets transmitted over a computer network or in the form of a computer program product stored on a disk, CD-ROM or any other data medium.

Although the invention was illustrated more closely and described in detail by way of the exemplary embodiments, the invention is not restricted to the disclosed examples and other variations may be derived therefrom by a person skilled in the art without departing from the scope of protection of the invention. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for evaluating an x-ray image of a breast produced during mammography, the method comprising:
   automatically producing, by a processor, a masking risk map for a region of the breast depicted in the x-ray image, wherein the producing takes into account a connectivity of dense breast tissue, and wherein the masking risk map comprises masking risk values that quantify a masking risk;

displaying the masking risk map on a screen together with the x-ray image, the masking risk map depicting areas of the dense breast tissue for varying levels of glandularity;

automatically determining, by the processor, the masking risk caused by mammographically dense tissue; and using the masking risk for one or more of categorizing, describing, or representing a breast density.

2. The method of claim 1, wherein data from a glandularity map is used for producing the masking risk map.

3. The method of claim 2, wherein the connectivity of the dense breast tissue is taken into account by applying a morphological opening method.

4. The method of claim 3, wherein a structure element used within a scope of the morphological opening method is disk-shaped and radii of structure elements used for ablation and addition differ from one another.

5. An apparatus for evaluating an x-ray image of a breast produced during mammography, the apparatus comprising:
a processor configured to:
produce a masking risk map for a region of the breast depicted in the x-ray image taking into account a connectivity of dense breast tissue, wherein the masking risk map comprises masking risk values that quantify a masking risk;
display the masking risk map on a screen together with the x-ray image, the masking risk map depicting areas of the dense breast tissue for varying levels of glandularity;
determine the masking risk caused by mammographically dense tissue; and
use the masking risk for one or more of categorizing, describing, or representing a breast density.

6. A non-transitory computer-readable storage medium stored on a computer for evaluating an x-ray image of a breast produced during mammography, the computer-readable storage medium comprising computer program instructions configured to, when executed on the computer, cause the computer to at least perform:
produce a masking risk map for a region of the breast depicted in the x-ray image taking into account a connectivity of dense breast tissue, wherein the masking risk map comprises masking risk values that quantify a masking risk;
display the masking risk map on a screen together with the x-ray image, the masking risk map depicting areas of the dense breast tissue for varying levels of glandularity;
determine the masking risk caused by mammographically dense tissue; and
use the masking risk for one or more of categorizing, describing, or representing a breast density.

7. The method of claim 1, wherein the conductivity of the dense breast tissue is taken into account by applying a morphological opening method.

8. The method of claim 7, wherein a structure element used within a scope of the morphological opening method is disk-shaped and radii of structure elements used for ablation and addition differ from one another.

9. The method of claim 1, further comprising:
automatically producing a masking risk value based on the masking risk map.

10. The method of claim 9, further comprising:
using the masking risk value to assign a breast density category to the region of the breast depicted in the x-ray image.

11. The method of claim 1, further comprising:
automatically producing a description of a position, a distribution, or both the position and the distribution of the mammographically dense tissue based on the masking risk map.

12. The method of claim 1, wherein the categorizing, describing, or representing the breast density comprises generating a breast density report.

* * * * *